(12) United States Patent
Du

(10) Patent No.: US 8,170,644 B2
(45) Date of Patent: May 1, 2012

(54) METHOD FOR FAST MULTI-SLICE MAPPING OF MYELIN WATER FRACTION

(75) Inventor: Yiping Du, Aurora, CO (US)

(73) Assignee: The Regents of the University of Colorado, Denver, CO (US)

( * ) Notice: Subject to any disclaimer, the term of this patent is extended or adjusted under 35 U.S.C. 154(b) by 619 days.

(21) Appl. No.: 12/297,482

(22) PCT Filed: Apr. 18, 2007

(86) PCT No.: PCT/US2007/066878
§ 371 (c)(1),
(2), (4) Date: Mar. 5, 2009

(87) PCT Pub. No.: WO2007/121472
PCT Pub. Date: Oct. 25, 2007

(65) Prior Publication Data
US 2009/0312625 A1     Dec. 17, 2009

Related U.S. Application Data

(60) Provisional application No. 60/792,851, filed on Apr. 18, 2006.

(51) Int. Cl.
*A61B 5/00* (2006.01)
(52) U.S. Cl. ........ 600/416; 600/410; 324/307; 324/309; 382/128
(58) Field of Classification Search .................. 600/410, 600/411, 407, 416; 324/307–310, 319; 382/128
See application file for complete search history.

(56) References Cited

U.S. PATENT DOCUMENTS

| 5,050,609 | A | * | 9/1991 | Balaban et al. ............ 600/410 |
| 5,560,360 | A | | 10/1996 | Filler et al. |
| 5,617,861 | A | | 4/1997 | Ross et al. |
| 6,463,315 | B1 | | 10/2002 | Klingberg et al. |
| 6,466,017 | B1 | * | 10/2002 | Ganin et al. ............ 324/318 |
| 6,529,763 | B1 | | 3/2003 | Cohen et al. |
| 7,034,531 | B1 | | 4/2006 | Tuch et al. |
| 2005/0065083 | A1 | | 3/2005 | Rueger et al. |
| 2005/0068031 | A1 | | 3/2005 | Frank |
| 2006/0080044 | A1 | * | 4/2006 | Ropele ............ 702/23 |

OTHER PUBLICATIONS

Lancaster JL, Andrews T, Hardies LJ, Dodd S, Fox PT. Three-Pool Model of White Matter. Journal of Magnetic Resonance Imaging. 17(1): 1-10.*
Kashmar GC, Nalciogly O, An Improved Echo Planar Reconstruction Method. IEEE Transactions on Nuclear Science. 35(1): 744-748.*

* cited by examiner

*Primary Examiner* — Brian Casler
*Assistant Examiner* — Amanda Lauritzen
(74) *Attorney, Agent, or Firm* — Snell & Wilmer L.L.P.

(57) ABSTRACT

Mapping of myelin water content in white matter may provide important information for early diagnosis of multiple sclerosis and the detection of white matter abnormality in other diseases. It is disclosed here that free induction decay (FID) of each voxel at multiple slice locations is acquired in the brain using an echo-planar spectroscopic imaging (EPSI) pulse sequence. The multi-slice EPSI acquisition is designed to have a short first echo time (~2 ms) and echo-spacing (~1 ms) in order to acquire multiple sampling points during the fast decay of the myelin water signal. Multi-compartment analysis is then applied to the FID in each pixel using a 3-pool model of white matter to obtain quantitative maps of the myelin water fraction. Using this technique, the MR data for whole brain mapping of the myelin water can be acquired in less than 10 minutes, making this technique feasible for routine clinical applications.

31 Claims, 15 Drawing Sheets

METHOD FOR FAST MULTI-SLICE MAPPING OF MYELIN WATER FRACTION

CROSS-REFERENCE TO RELATED APPLICATIONS

This application claims priority to PCT Application Number PCT/US2007/066878, filed Apr. 18, 2007 and U.S. Provisional Patent Application Ser. No. 60/792,851 filed Apr. 18, 2006.

FIELD OF INVENTION

The present disclosure relates to the field of magnetic resonance imaging ("MRI"). In particular, it relates to brain imaging using MRI techniques and methods to collect and quantitatively analyze the magnetic resonance data.

BACKGROUND OF THE INVENTION

Healthy neuron axons in the brain are wrapped by myelin sheath, which is formed by fatty layers of myelin. The myelin sheath is critical for the communication of bioelectric signal among different regions of the brain. Myelin can increase the speed at which signals travel between brain cells by up to 100-fold compared to axons lacking myelin. Destruction of the myelin sheath, a.k.a. demyelination, can impair brain functions and is considered a primary pathology of several white matter diseases, such as multiple sclerosis (MS) and leukoencephalopathies. Impaired myelination is also considered as an important pathology in Alzheimer's disease and several psychiatric disorders, such as schizophrenia and autism.

Multiple Sclerosis (MS) is an inflammatory disease of the central nervous system (CNS), which includes the brain and the spinal cord. Demyelination of white matter (WM) in the CNS is considered a major pathological factor for MS. MS is believed to be an autoimmune disease in which the immune system attacks a component of myelin in the central nerve system. T cells, which are one type of white blood cells in the immune system, become sensitized to myelin and cross the blood-brain barrier into the central nervous system, causing damages to myelin and axons. Demyelination can occur much earlier than the time when MS can be diagnosed using current diagnostic standards. One study found only 2% myelin content in an MS lesion compared to 10% in normal-appearing WM. Low myelin content in MS lesions has also been verified by post-mortem studies. Demyelination has also been suggested to be the dominant feature of normal-appearing WM pathology in MS. The identification of demyelination can be used as a significant predictor of the prognoses of the clinically isolated syndrome and for earlier diagnosis and treatment of MS. Quantitative measurement of remyelination would allow physicians to assess the effectiveness of treatment.

Demyelination has also been found to be related to Alzheimer's disease. A recent study suggests that demyelination, along with axonal degeneration, may be the cause for the observed increase of apparent diffusion coefficients in hippocampus and corpus callosum of patients with mild cognitive impairment. In addition, recent diffusion tensor imaging (DTI) studies found reduced fractional anisotropy in the frontal and temporal WM in mild cognitive impairment and early Alzheimer's disease. A post-mortem neuropathological study has confirmed the reduction of myelin density in Alzheimer's disease. Substantial recent evidence also suggests that dis-regulation of myelination is associated with schizophrenia, autistic disorder, and development disorders. In fact, one study found that the left corpus callosum in genu had 36% lower myelin content in schizophrenia patients than in healthy volunteers.

MRI has been used to detect pathology including focal and diffuse hyperintense lesions, hemorrhage, and atrophy with greater sensitivity than computed tomography. Although MRI provides excellent anatomic details, interpretation of MRI results is influenced by the experience and skill of the interpreter. A quantitative characterization of the raw data can provide a more objective reflection of the physiological status of the subject. For instance, MRI can provide quantitative data regarding the relaxation properties of water in different chemical environments induced by inflammatory diseases of the brain. The spin-lattice (T1) and spin-spin relaxation times (T2) provide information regarding the total water in brain, the compartmentalization of brain water, and the degree of association between this water and macromolecules such as myelin and protein.

Several MRI techniques have been used to detect signal changes that may be associated with demyelination in MS. The Magnetization Transfer (MT) technique has been used to measure the fraction of protons in a semisolid pool, $f_b$, which contains protons bound to macromolecules (such as myelin), relative to the protons in a free pool (mostly in water) using the various models. Studies have shown a reduction of $f_b$ in MS lesions and normal appearing white matter (NAWM) compared to control WM. Although $f_b$ can be used as an indicator of myelin integrity, it is not a direct measurement of myelin water fraction (MWF), because myelin is not the only macromolecule presented in WM or gray matter (GM). Moreover, correlations between the semisolid proton fraction and myelin and axonal density have not been well established.

Another approach is called diffusion-weighted imaging (DWI), which attempts to characterize tissues based on the random translational motion of water protons. In biological tissue, normal hindrance of the mobility of water protons occurs from structural elements such as cell membranes and subcellular organelles. Thus, the mobility of water protons differs from organ to organ. Pathologic processes tend to alter the magnitude of this organization by either a destruction or reduplication of membranous elements or by a change in cellularity, e.g., scarring, inflammatory, or neoplastic infiltration. Shifts in the number of water protons between tissue compartments may be caused by changes in permeability, osmolarity, active transportation or other alterations. All these alterations may have an impact on proton mobility or diffusivity. Because these movements may occur in all directions, they are termed isotropic diffusion.

In normal tissues, a directional portion of diffusion, called diffusion anisotropy, may exist which is associated with the presence of tubular structures such as neuronal fibers. This anisotropy derives from the fact that water molecules move more readily along a fiber than perpendicular to the fiber. Myelinated fibers, such as those in the brain, exert strong anisotropic effects due to their multiple circular lipid bilayers, and this phenomenon increases with the density of fibers running in parallel. Therefore, a decrease in diffusion anisotropy may signal structural disintegration of the brain. Specifically, this indicator may be used not only to detect damage to major neuronal pathways focally, but also to detect damage remotely for lesions caused by degeneration.

Accurate determination of the complete diffusion information requires DWI with at least six diffusion-encoding gradient directions followed by a series of calculations called diffusion tensor imaging (DTI). DTI has recently been used to assess the integrity of myelin sheaths and axons by measuring the fractional anisotropy (FA) of diffusion tensor, which indicates the degree of cylindrical confinement of the water in intra- and extra-axonal spaces. WM tractography with DTI which has been used to evaluate the axons passing through local MS lesions, may potentially provide a better understanding of damage to myelin sheaths and axons and predict the development of disability. Recent animal studies using DTI also provide strong evidence that the increase in diffusivity in a direction perpendicular to the axons indicates the break down of myelination, while the decrease in diffusivity in a direction parallel to the axons indicates the presence of axonal damage.

While DTI may provide significant insights to the pathology of MS and may potentially differentiate axonal damage from demyelination, the complexity of axonal tracks, such as fiber-crossing, may introduce substantial errors in DTI-based measurements, or even render such measurements less meaningful in many regions of the brain. In addition, diffusion anisotropy serves as an indirect indicator of the maturity and integrity of WM, rather than a direct physiological measurement.

By contrast, quantitative mapping of MWF is a direct measurement of the amount of myelin in WM. It may provide a direct indicator of the integrity of the myelin sheath and may offer valuable insights into the pathology of focal lesions and NAWM. A successful technique for quantitative mapping of the MWF was developed by MacKay et al. This technique uses a 32-echo Carr-Purcell-Meiboom-Gill (CPMG) technique to acquire the MRI signal of white matter. A nonnegative least squares (NNLS) algorithm is then used to estimate the MWF from the compartment with a short T2 decay constant. This technique demonstrates the merit of quantitative measurement of MWF in studying the pathology of MS. However, at least three major issues are associated with this technique.

First, it is difficult to shorten the first echo time (TE1) and echo spacing (ES) with the CPMG technique. With the TE1 and ES values that are typically used, the myelin water signal with T2 at 15 ms is only effectively detected in the first 2-3 measurements (i.e., first 2-3 echoes), leading to compromised accuracy in estimating the MWF using multi-exponential fitting. For example, the myelin signal with T2 at 15 ms is reduced to 51% at the 1st echo, 26% at the 2nd echo, and 13.5% at the 3rd echo with TE1 at 10 ms and ES at 10 ms. In this technique, the T2 decay is acquired at each pixel using a train of non-selective inversion pulses. The TE1 of the echo train is 10 ms and the ES is 10 ms, allowing the acquisition of only a few time points during the decay of the myelin water signal. An average of four scans is usually needed (at 1.5 T) with a total scan time of 25-28 minutes to increase the signal-to-noise ratio ("SNR") for data analysis. In addition, with the relatively long TE1 and ES, the detected myelin water signal is more heavily weighted by the myelin water with a longer T2 (15-40 ms).

Secondly, the CPMG technique acquires signals from one slice during a 25-28 minute scan, making it difficult to analyze multiple lesions that cannot be evaluated by a single slice. While this technique has proven to be effective in detecting the demyelination in MS lesions and normal appearing white matter, the lack of volume coverage, as well as the long image acquisition time, has severely limited the use of this technique in the research and clinical diagnosis of MS.

Lastly, the accuracy of the MWF measurements may be compromised because the T2's of myelin water are not well defined using the NNLS algorithm. For the T2 range of myelin water (10 ms<T2<50 ms) used in the NNLS algorithm, a substantial "signal leakage" between myelin water and myelinated axon water (T2~40 ms; T2=29.7 ms (Bovine optical nerve samples, 7 Tesla)) may occur due to possible overlap of their T2 ranges.

In summary, the current MRI technique for myelin mapping is not adequate for routine clinical exams and neurological studies due to its long imaging time and reduced volume coverage. A direct and quantitative mapping of myelin content which overcomes these inadequacies could be used in (1) early characterization and diagnosis of MS; (2) differentiation of demyelination and axonal damages in MS lesions; (3) exclusion of inflammation-induced hyperintensity foci in T2 MRI from demyelination pathology; (4) assessment of the myelination in patients with psychiatric disorders; (5) longitudinal studies of WM maturation in children and adolescents; and (6) longitudinal studies of neuro-degeneration in elders, such as Alzheimer's disease.

Therefore, there remains a need for a quantitative method for multi-slice mapping of myelin water fraction that may be completed within a short period of time. There is a further need for a method to process data by reducing the "signal leakage" between myelin water and myelinated axon water.

SUMMARY OF THE INVENTION

The present disclosure solves these problems by using echo-planar spectroscopic imaging (EPSI) to acquire the free induction decay (FID) of each voxel at multiple brain slice locations. The acquired data are further processed using a 3-pool model of white matter to obtain quantitative maps of MWF. It is an objective of this invention to develop a new imaging technique and data analysis tool for multi-slice quantitative mapping of MWF in a subject's brain within a clinically acceptable imaging time.

It is another objective of this invention to substantially increase the number of measurements before the decay of the myelin signal. It is yet another objective to increase the volume coverage and reduce the imaging time to less than 10 minutes by using multi-slice data acquisition. It is yet another objective of the invention to reduce the "signal leakage" between myelin water and myelinated axon water in the multi-compartment analysis.

The present disclosure uses an EPSI sequence for data acquisition. By using the EPSI sequence, the TE1 may be reduced to 2.2 ms with the ES value reduced to 1.2 ms. Using these shortened TE1 and ES values, the signal of myelin water with $T2^*=15$ ms is at 87% at the first measurement and at 36.7% at the 12th measurement (i.e., 12th echo). MWF is calculated using multi-exponential analysis with a 3-pool model. In addition, the acquisition of $T2^*$ free induction decay requires much lower radio frequency ("RF") power deposition than the acquisition of T2 decay and is therefore more suitable for data acquisition under strong (3.0 Tesla and higher) magnetic fields.

Whole brain MWF maps also provide valuable pathological insight in WM diseases related to dysmyelination or demyelination, such as MS. Although both demyelination and axonal damage may be related to the prognosis of MS, previous studies have suggested that demyelination is reversible while axonal damage is not. Thus, differentiating demyelination and axonal damage becomes clinically relevant and may provide guidance to the therapeutic treatment of MS. Using the 3-pool model, it is feasible to identify the area of the lesions wherein demyelination or axonal damage is the primary pathology.

Acquiring $T2^*$ decay has the advantage of increasing the volume coverage, because the length of sequence for each k-space line with EPSI acquisition can be greatly reduced due to the fact that T2* decay in WM is approximately two times faster than T2 decay. In previously used MRI techniques, 32 echoes were acquired with a duration of data acquisition duration at 320 ms for each k-space line. In the presently disclosed implementation of the EPSI sequence, 126 echoes are acquired in less than 150 ms for each k-space line. This reduced duration for data acquisition allows the acquisition of one k-space line for up to 12 slices with a repetition time (TR) of 2 seconds.

DETAILED DESCRIPTION

Figure 1:
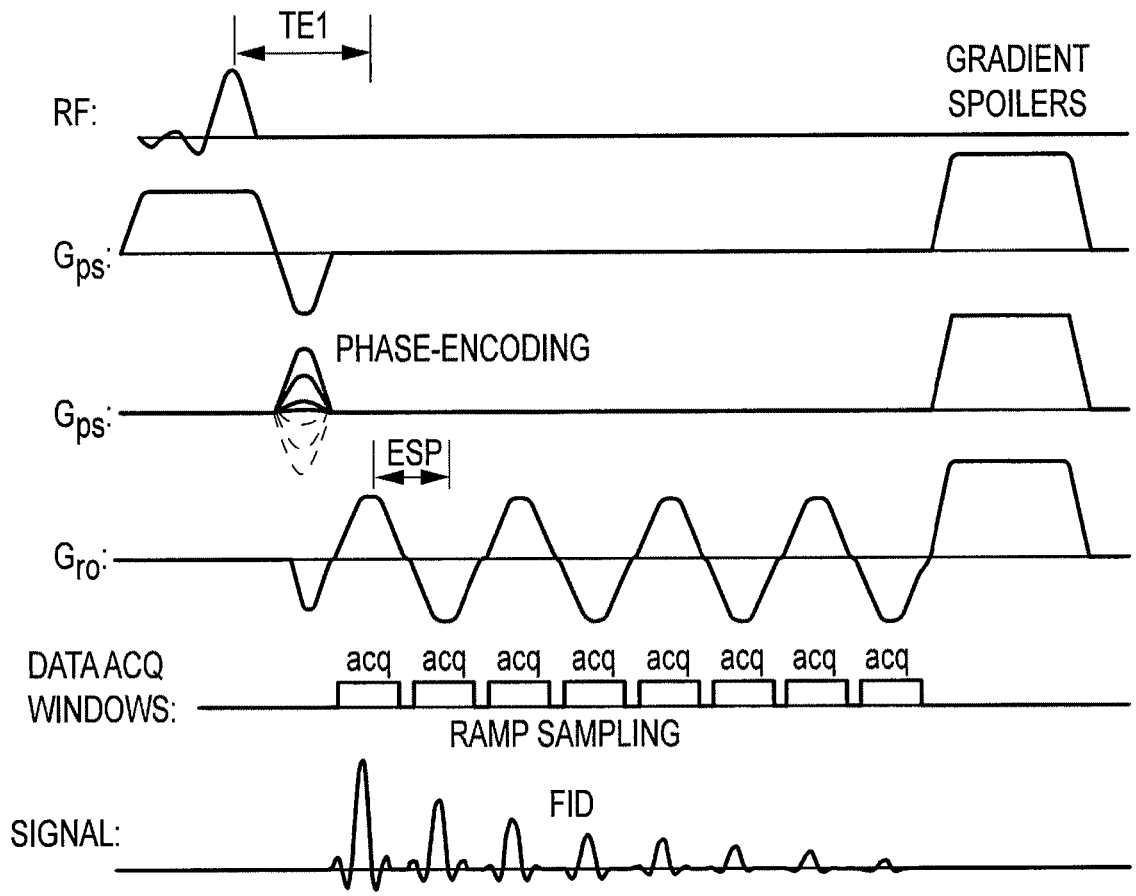
FIG. 1 is a diagram of an EPSI (a.k.a. multi-gradient-echo pulse sequence) with minimal TE1 and ramp sampling in accordance with the present invention.

For purpose of clarity, it is helpful to define some terms used in this disclosure. It should be appreciated that the following definitions are used throughout this application. Where the definition of terms departs from the commonly used meaning of the term, the definitions provided herein should be used in interpreting the present disclosure, unless specifically indicated otherwise.

For purpose of the present invention, the terms "subject" and "individual" are used interchangeably to refer to either a person or an animal. The term "MRI" refers to any imaging technique utilizing magnetic resonance to analyze an individual's body or any part thereof.

A "voxel" is a volume element, representing a value in three dimensional space. The value of a voxel may represent various properties in different applications.

In the 3-pool model, WM tissue consists of a myelin (my) pool, a myelinated axon (ma) pool, and a mixed (mx) pool. This model was originally applied to the measurements of T2 decay, with the T2 range of 10 ms for the my pool, 40 ms for the ma pool, and 130 ms for the mx pool at 1.9 T. A modified 3-pool model is used for the measurement of T2* decay, accounting for the difference between T2* decay and T2 decay. The T2* relaxation time in a pixel is related to the T2 relaxation time by:

$$1/T2^* = 1/T2 + 1/T2' \quad \text{[I]}$$

where T2' is a time constant inversely proportional to the local magnetic field inhomogeneity. The T2' in WM at 3 Tesla is estimated to be approximately 100 ms, based on the documented T2 (79.6 ms) and T2* (44.8 ms) of WM. Assuming that T2' is the same in all three pools, the estimated T2* value would be 9.1 ms in my, 28.8 ms in ma, and 57.3 ms in mx, respectively. Apparently, the shortening of T2* compared to T2 is much smaller in the my pool than in the other two pools, a feature that is advantageous to the detection of myelin water signal. This simple analysis indicates that the 3-pool model is applicable to T2* measurements because the T2* values of these 3 pools remain separated and the T2* of myelin water remains in the range suitable for detection.

In the present disclosure, MWF may be calculated using the T2*-based 3-pool model with 7 unknowns:

$$S(t) = A_{my} e^{-t/T2^*,my} + A_{ma} e^{-t/T2^*,ma} + A_{mx} e^{-t/T2,mx} + A_{b1} \quad \text{[II]}$$

where the $A_{my}$, $A_{mn}$, and $A_{mx}$ represent the amplitudes of the signal arising from 3 water pools, and $A_{b1}$ represents any residual baseline signal. After fitting the measured FID with the 3-pool model, MWF is estimated as:

$$MWF = A_{my}/(A_{my} + A_{ma} + A_{mx}) \quad \text{[III]}$$

Due to the increased SNR under stronger magnetic field, it is desirable to conduct the MWF mapping under relatively high magnetic field strength (3 Tesla and higher). The disclosed EPSI technique is more suitable at high magnetic field than the CPMG technique for two reasons. First, the EPSI data acquisition employs only one 90-degree RF pulse in the sequence and the CMPG data acquisition employs a train of 180-degree inversion pulses. Therefore, it is more challenging to keep the specific absorption rate (SAR) of the CPMG acquisition under a level considered safe to human subjects at high fields. Secondly, the length of echo train can be shortened with EPSI acquisition because of the reduced T2* at higher field, while T2 is independent of the field strength. The decrease of T2* allows a reduced TR without increasing residual transverse magnetization. In addition, the increased SNR at higher magnetic field strength also reduces the need for multiple averaging in data acquisition.

The imaging time for the whole brain mapping of MWF may be further reduced by using the EPSI data acquisition. Two approaches may be taken to reduce the imaging time. First, the TR may be reduced without considerable reduction of myelin water signal, because of the short T1 value (350 ms at 3 Tesla). Using a shortened TR (e.g., TR=1 s) may increase the partial saturation of the signal from the myelinated axonal water (T1=850 ms) and the signal from the mixed water (T1>1000 ms). Therefore, shorter TR may increase the relative amplitude of signals originating from the myelin water.

In one exemplary embodiment, a post-mortem brain acquired from a subject with focal MS lesions was scanned. The subject had a history of MS symptoms, and no other neurological impairment had been recorded. The brain had been fixed with 10% formalin for 3 years prior to the scan. The brain was placed in a water-filled container for scanning after air bubbles had been carefully removed.

The T2* FID in each pixel is detected using EPSI acquisition on a 3 Tesla MRI scanner (General Electric, Waukesha, Wis.) equipped with high performance gradient coils (maximum gradient amplitude of 43 mT/m and maximum slew rate of 150 T/m/s). In the EPSI pulse sequence, a minimum-phase Shinnar-Le Raux excitation pulse of 3.2 ms is used to minimize the first echo time (TE1. The echoes may be acquired on both the flat-top and ramps of the readout gradient waveform in order to further shorten the TE1 and echo spacing (ES) as shown in FIG. 1. Gradient spoilers were applied to all three axes to reduce the residual transverse magnetization. In one exemplary embodiment, a 126-echo EPSI sequence is used with an image matrix of 256×256, TE1 of 2.1 ms, and ES of 1.1 ms, the other imaging parameters are: 20 cm field-of-view (FOV) and 5 mm slice thickness with a 1 mm gap between slices. Using a TR of 2 seconds, up to 12 slices may be acquired to cover the brain with an imaging time of 8.7 minutes.

The k-space data may be reconstructed into the (x, y, t) domain on an off-line computer using a reconstruction software developed for this purpose. The field inhomogeneity introduced by the subject may cause a mismatch of the echo centers between the even and odd echoes. This echo center mismatch may result in an image ghost in the phase-encoding direction in conventional echo-planar images. The echo center mismatch is manifested as spectral ghosting in the EPSI. In order to minimize the possible adverse effects the echo center mismatch has in the $T2^*$ relaxation measurements, a Fourier transformation may be used to convert the data at each pixel into water resonance in the temporal frequency domain. The even and odd echoes are aligned to minimize the amplitude of the spectral ghost. An inverse Fourier transform may be then applied to the corrected water resonance to obtain the corrected $T2^*$ relaxation.

A quasi-Newton algorithm in Matlab for multi-variable optimization may be used to minimize the root-mean-squared (RMS) error between the measured signal and fitting in the multi-compartment analysis. The compartment with a $T2^*$ range of 3-16 ms is considered as the my pool, 16-36 ms as the ma pool, 36-160 ms as the mx pool. These selections of $T2^*$ range are based on a previous experiment conducted using bovine optical nerve samples at 7 Tesla in which T2 was determined to be 7.1 ms (SD=2.3 ms) for the my pool, 27.7 ms (SD=7.0 ms) for the ma pool, and 66.6 ms (SD=1.3 ms) for the mx pool. In addition, the shortening of T2 caused by the fixation of brain tissue is also considered. The individual water fraction maps of these 3 pools may be visually inspected to validate the selection of these $T2^*$ ranges.

Figure 3:
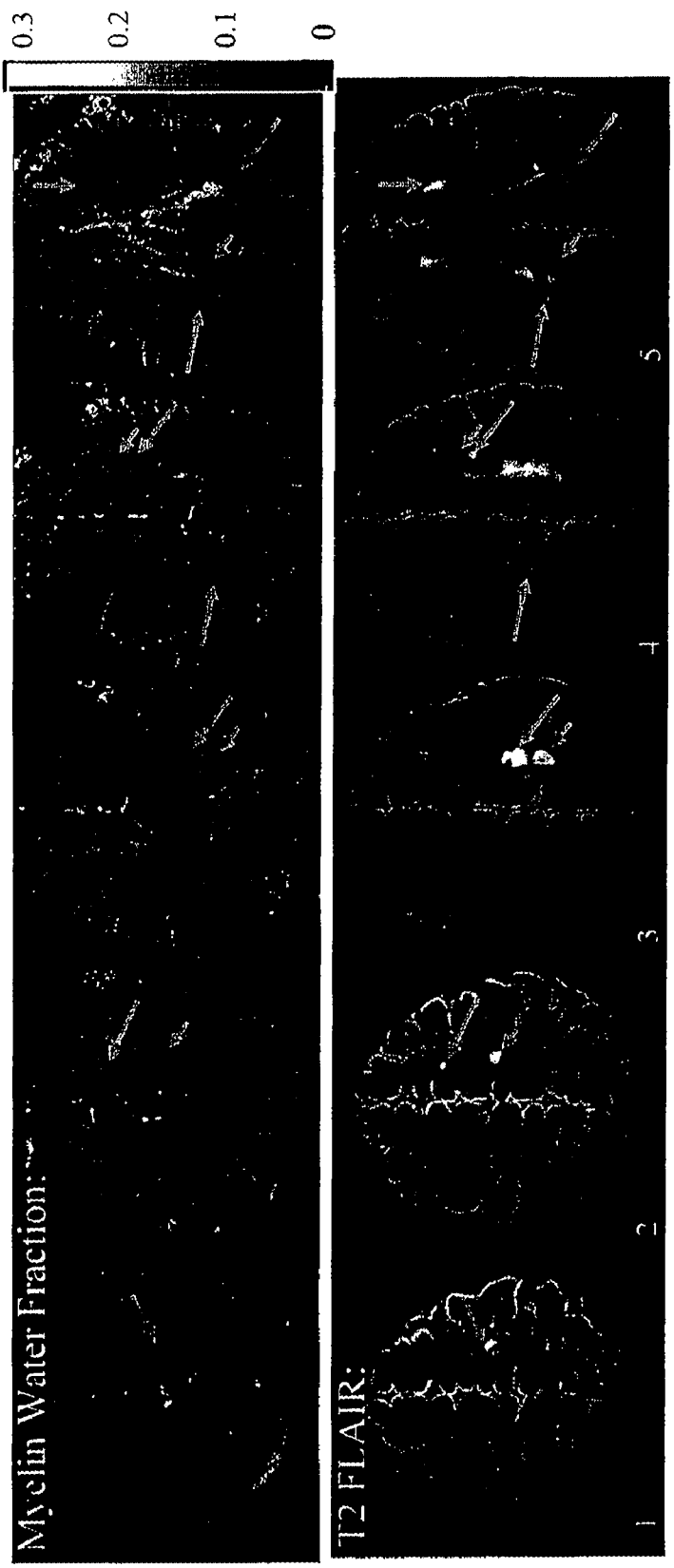
FIG. 3 shows five MWF maps from a fixed MS brain (top) and T2-FLAIR images acquired at the same slice locations (bottom).

FIG. 3 shows 5 MWF maps from a fixed MS brain (top) and T2-FLAIR (for "Fluid Attenuated Inversion Recovery") images acquired at the same slice locations (bottom). The signal from myelin water is reliably detected in regions of normal appearing white matter in all these slices. The MWF is substantially reduced, or nearly undetectable at the locations of focal MS lesions, as indicated by the arrows. Several small lesions shown in the T2 FLAIR images are well depicted in the MWF maps (e.g., the lesions indicated by the arrows at the 41 h slice). Expected differences in myelin content of normal regions of gray and white matter are also apparent in these MWF maps.

Figure 4:
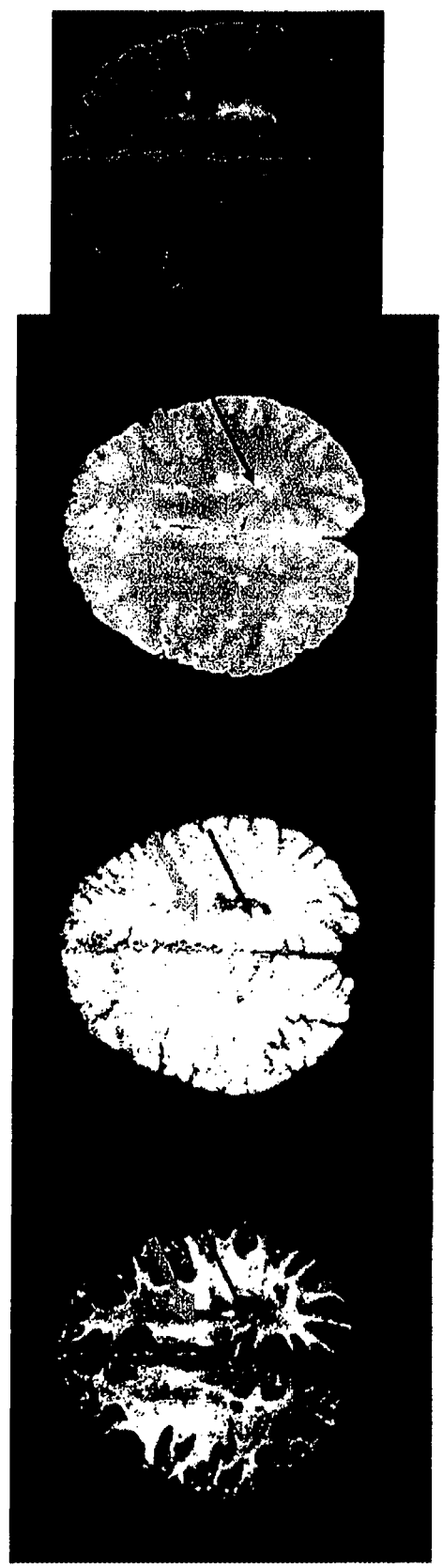
FIG. 4 shows the maps of the myelin pool (a), myelinated axon pool (b), and mixed pool (c).

FIG. 4 shows the maps of the my pool (a), the ma pool (b), and the mx pool (c) at slice 4. The ma and mx maps show well delineated GM, WM, and MS lesions. The $T2^*$ of GM appears to be in the range of the ma and mx pools, resulting in higher intensity in the ma and mx maps. The center of the lesion, as indicated by the short arrow, appears to have much lower intensity in the my and ma pools, suggesting the occurrence of both demyelination and axonal damage. On the other hand, the periphery of MS lesions, indicated by a long arrow, have lower intensity in the my pool, indicating the occurrence of demyelination. The periphery of MS lesions, however, has higher intensity in the ma pool, suggesting that axonal damage is unlikely to be a major contributor to the pathology. It is noticed that the central lesions have a higher intensity than the periphery of the lesions in the mx pool, again suggesting that axonal damage is less likely to occur at the periphery of the lesions. Previous studies indicate that the pathology of demyelination may be reversed by remyelination, while axonal damages are irreversible. The 3-pool modeling may provide a direct indicator that would differentiate axonal damage from demylination.

Figure 5A:
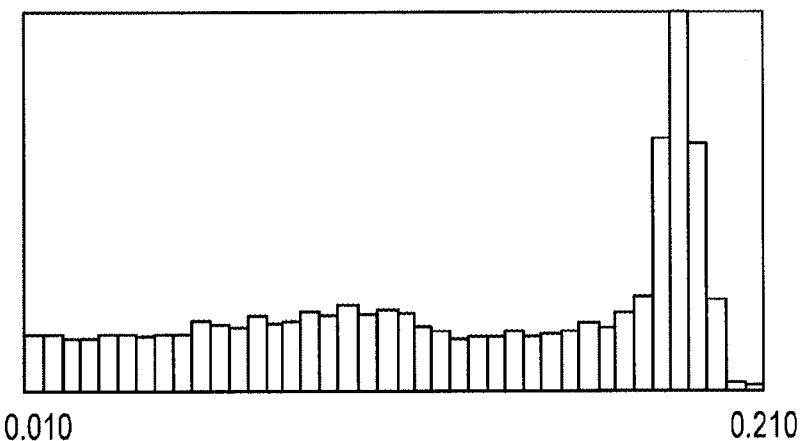
FIG. 5 shows the histograms of MWF, myelinated axon, and mixed water in the brain.
Figure 5B:
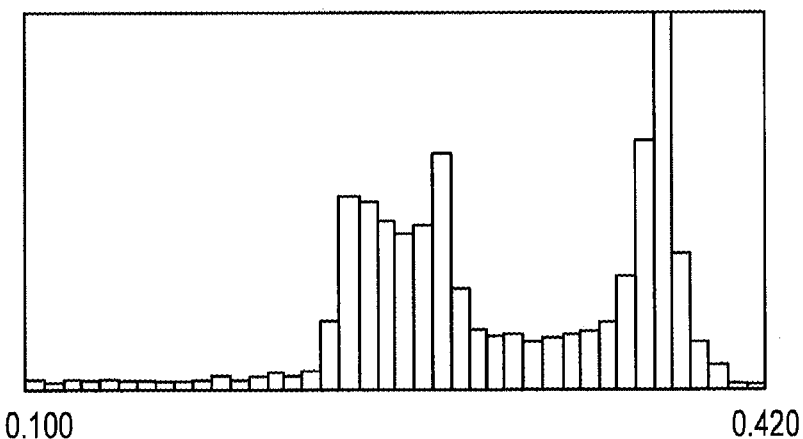
Figure 5C:
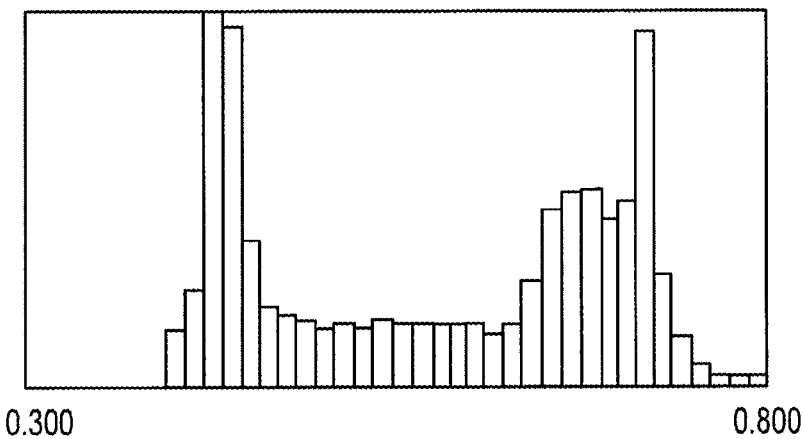

FIG. 5 shows the histograms of MWF in these brains. FIG. 5(a) shows that the MWF is in a range below 20% and peaks at 18.5%, consistent with previously reported measurements. The histogram of myelinated axon FIG. 5(b) shows two peaks corresponding to WM (right) and GM (left). The histogram of the mixed water pool in FIG. 5(c) also shows two peaks corresponding to GM (right) and WM (left).

Figure 6:
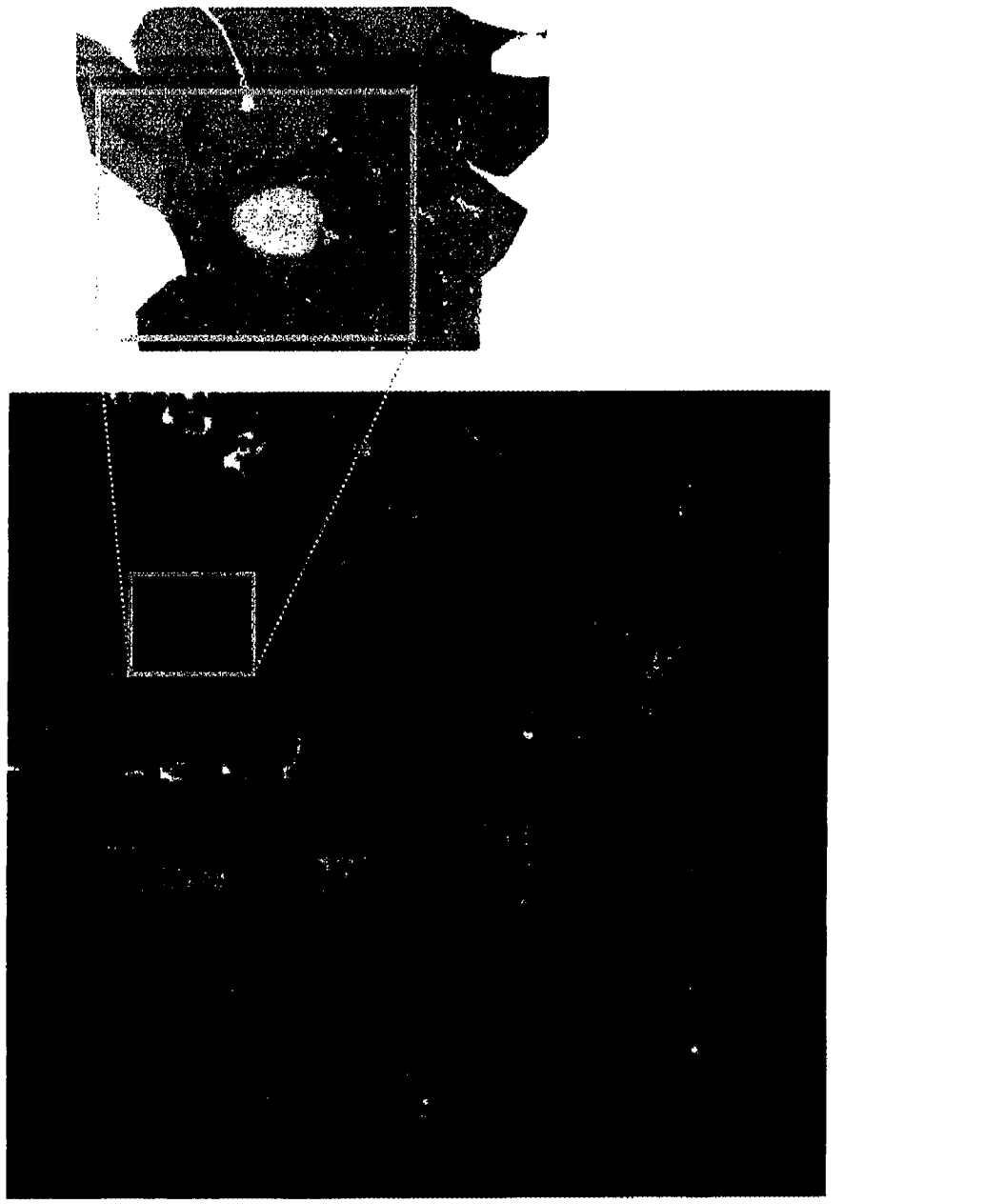
FIG. 6 shows the histopathology of the brain tissue near a lesion.

FIG. 6 shows the histopathlogy of the brain tissue near a lesion in slice 3, as indicated by arrows in FIG. 3. The histopathology of the MS lesion (right panel) confirms the demyelination at the region where the MWF map (left panel) show diminished intensity, as indicated by the "hole" with lighter color at the center of the rectangular inset.

The data shown above were acquired from a fixed brain. There may be additional technical challenges in applying the disclosed method to in vivo mapping of MWF. The motion of a subject during the EPSI data acquisition, such as gross motion of the head, respiratory motion of the chest, and cardiac pulsation of the arteries in the brain, and pulsation of the cerebralspinal fluid (CSF), may introduce errors in the FID measurements. The gross motion of the head may be measured and corrected using a navigator echo technique. For instance, one navigator echo may be acquired after the echo train at the readout gradient to detect the translational motion in the readout direction; another navigator echo can be acquired after the echo train at the phase-encoding gradient to detect the translational motion in the phase-encoding direction. In addition, the effect of cardiac pulsation on the arteries in the brain may be reduced by using cardiac triggering or cardiac gating. The flow effects of the blood and CSF may be suppressed by applying inversion RF pulse(s) prior to the EPSI sequence.

It is also known that respiratory motion of the chest can cause fluctuation of the main magnetic field, usually annotated as B0, in the brain, which may introduce errors in the Fill measurement. The EPSI sequence without pre-phaser and phase-encoding, which is known as a reference scan, may be used to detect the temporal fluctuation of B0. The reference scans maybe applied to a slice location above the imaging volume and another slice location below the imaging volume within a TR for the detection of the respiration-induced B0 change. The respiration-induced errors in the FID in each voxel may be reduced by correcting the respiration-induced phase errors in the data acquisition.

In another exemplary embodiment, brains of healthy subjects were scanned with a 128-echo multi-gradient-echo sequence on a 3 Tesla MRI scanner manufactured by General Electric as previously described above to record the $T2^*$ decay curve. Eight slices were acquired (up to 18 slices are possible) with a matrix of 128×128, a slice thickness of 3 mm, and a FOV of 20 cm. TR was 2 s, flip angle was 90 degrees, the first echo was at 2.124 ms, and echo spacing was 0.776 ms. A three-pool model was used for multi-exponential fitting to estimate MWF from the decay measurements and the local gradient compensation was incorporated. The three-pool model consisted of a myelin (my) water pool, a myelinated axon (ma) water pool, and a mixed (mx) water pool. Since T2* decay measurements for some tissues are affected by the susceptibility-induced local gradients, a compensation method using a sin c function was incorporated into the multi-exponential fitting procedure. The susceptibility effect was corrected for by modeling local susceptibility field gradient (SFG) in the 3-pool model as follows:

$$S(t) = \sin c((\gamma/2\pi)G_s t\Delta z)(A_{my}e^{-t/T2^*my} + A_{ma}e^{-t/T2^*ma} + A_{mx}e^{-t/T2^*mx} + A_{b1}) \quad (IV)$$

where $G_s$ is the amplitude of the SFG and is a variable in the optimization procedure.

Figure 7:
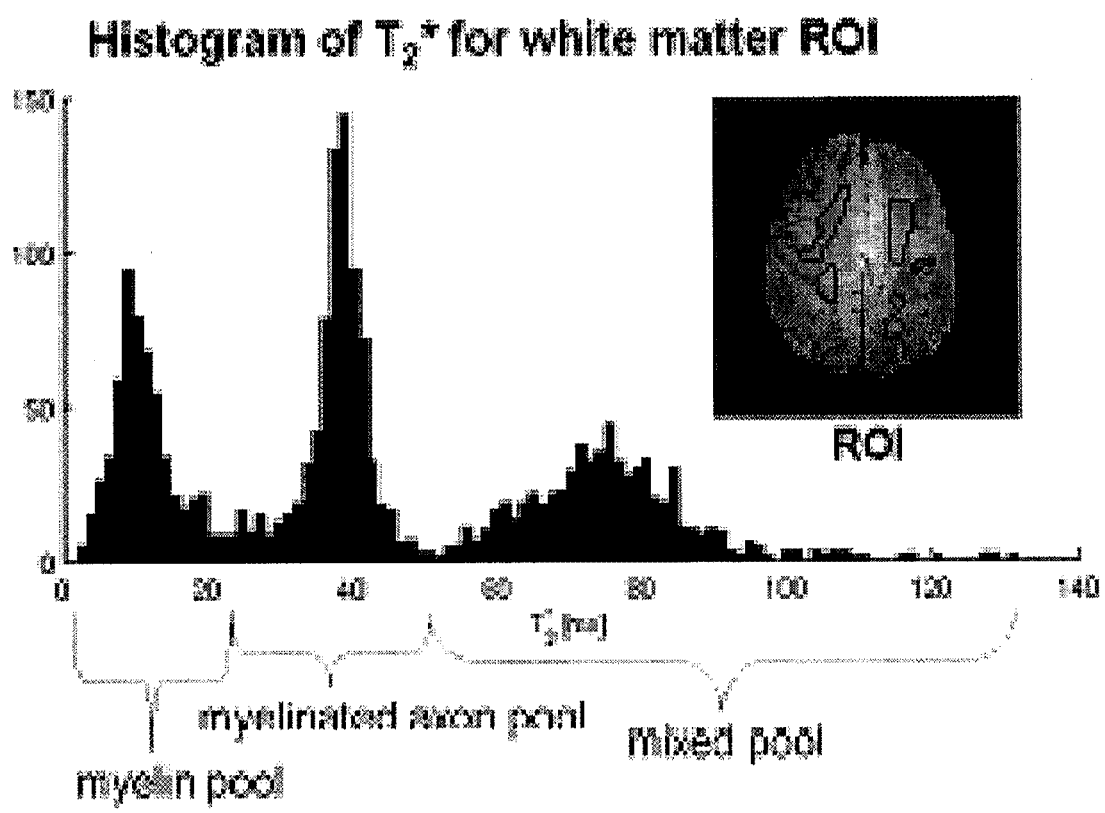
FIG. 7 shows a histogram of T2* over the regions of interest in white matter of living brains.
Figure 8:
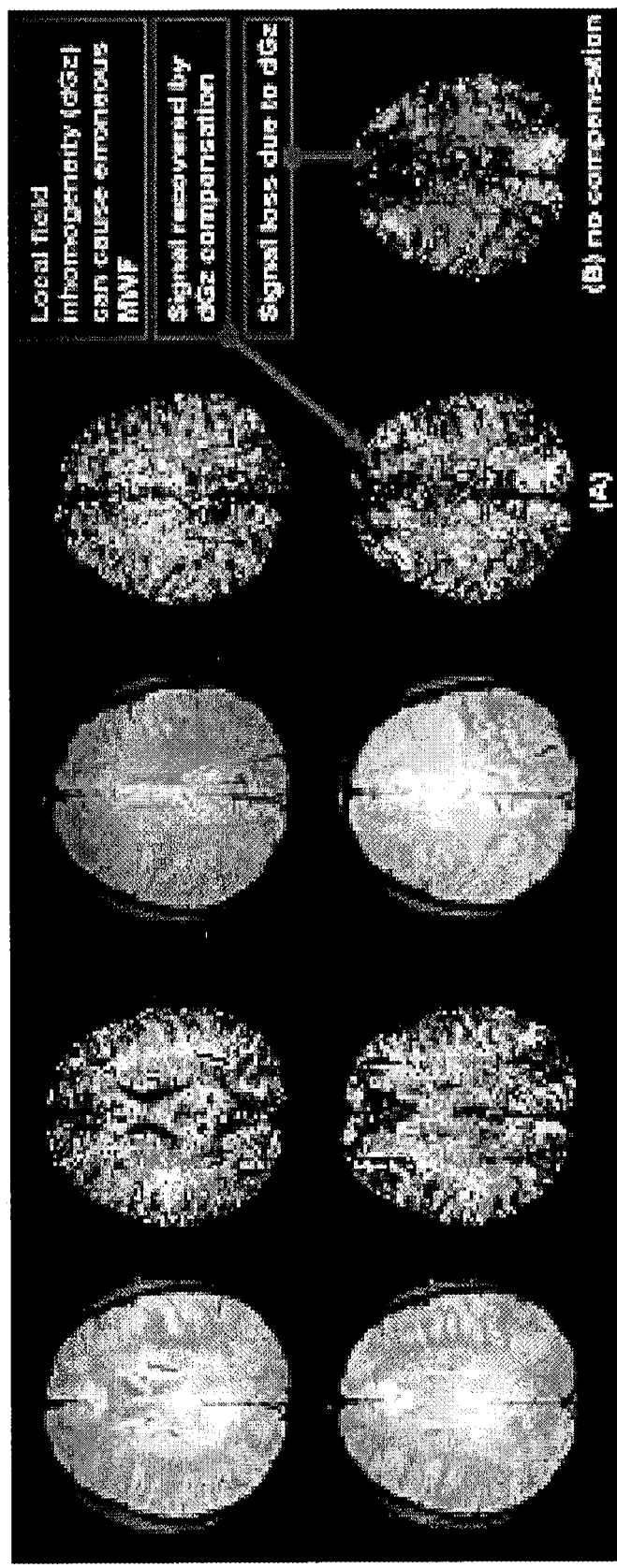
FIG. 8 shows the MWF maps of the upper 4 slices of a living brain based on the T2* ranges shown in FIG. 7.

FIG. 7 shows a histogram of T2* over the regions of interest in white matter. The three distinct peaks correspond to the myelin water pool (3~22 ms, the myelinated axon water pool (22~50 ms), and the mixed water pool (50~132 ms), respectively. The upper 4 slices of the brain were analyzed based on these T2* ranges and their MWF maps were estimated as shown in FIG. 8. The rightmost column of FIG. 8 explains the effect of the susceptibility-induced local gradients on MWF mapping. The bottom image (B) is the MWF map estimated without the local field compensation and the MWF at the orbitofrontal region was significantly reduced. In contrast, the map estimated with compensation (A) shows the recovered MWF on that region.

Figure 9:
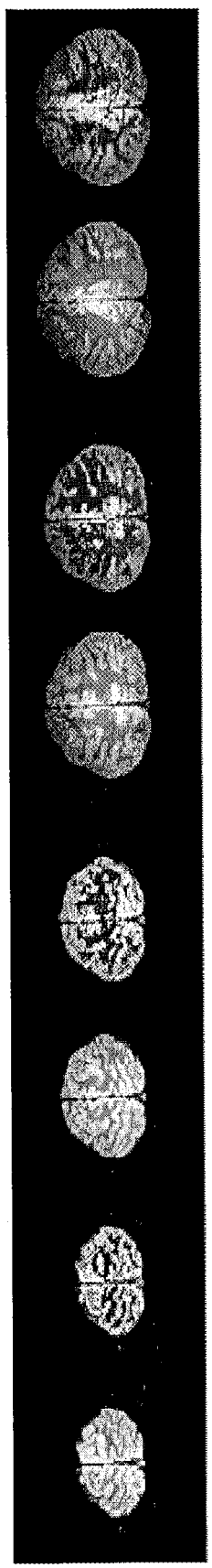
FIG. 9 shows MWF maps for another living brain.

FIG. 9 shows MWF maps for another living brain. Only high MWF (>0.15) are shown, overlaid on anatomical images. In this exemplary embodiment of preliminary results of MWF mapping using T2* relaxation applied to living brains as shown in FIGS. 7-9, it was expected that T2* ranges would be longer than those of fixed post-mortem brains considering the T2 shortening effect due to the tissue fixation. As expected, T2* ranges for living brains were estimated to be 3~22 ms, 22~50 ms, and 50~100 ms for myelin, myelinated axon, and mixed pools, respectively, while the T2* ranges for fixed brains were 3~16 ms, 16~34 ms, and 34~45 ms for myelin, myelinated axon, and mixed pools, respectively. The sin c function was used as a compensation method in living brains to reduce the effect of the susceptibility-induced local gradients. The sin c function approach assumed that the local gradient was linear in the z-direction. These results have demonstrated the new multi-slice technique of the present invention to estimate MWF using T2* relaxation, which makes the acquisition much faster (8.7 minutes for up to 12 slices) with finer temporal resolution (128-echo measurements with the first echo at 2.1 ms and 1.1 ms intervals) than the previous approaches with T2 relaxation.

In yet another exemplary embodiment, post mortem brains were scanned to optimize the range of T2* values for each pool in the multi-compartment analysis of myelin water fraction mapping. The multi-gradient-echo sequence was used to record the T2* decay curve and the three-pool model was used to analyze the decay measurements for quantitative mapping. Post-mortem brains were scanned with a 128-echo multi-gradient-echo sequence on a General Electric 3T scanner as previously described. Images with 256×256 matrix were acquired with a slice thickness of 5 mm and a FOV of 30 cm. TR was 2 s and flip angle was 90 degrees. The three-pool model consisted of a myelin (my) water pool (T2*<$t_1$), a mylenated axon (ma) water pool ($t_1$<T2*<$t_2$), and a mixed (mx) water pool ($t_2$<T2*). The proper selection of ($t_1$,$t_2$) is important for reliable fitting results. If $t_1$ is set too small, a large portion of myelin water signals leak into the myelinated axon pool, resulting in underestimation of MWF and a higher fitting error. If $t_1$ is set too high, some portion of mylenated axon water signals leak into the myelin pool, resulting in overestimation of MWF and a higher fitting error due to misfitting the myelinated axon pool. The optimal ($t_1$, $t_2$) where the rate of change of the measured MWF (i.e. the derivative d(MWF)/dt) as well as the fitting errors were minimized was found to be where $t_1$ was 16-20 ms and $t_2$ was 36 ms.

Figure 10:
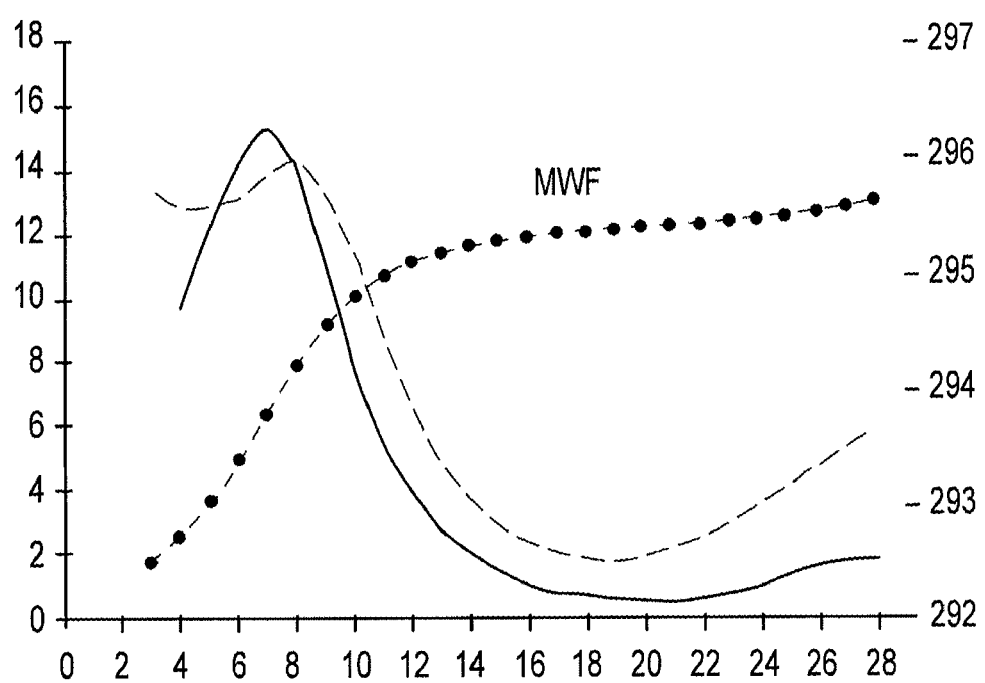
FIG. 10 is a graph showing the average MWF measurement at a white matter region for fixed post mortem brains, its variation over $t_1$, and the fitting error for different $t_1$ values.
Figure 11:
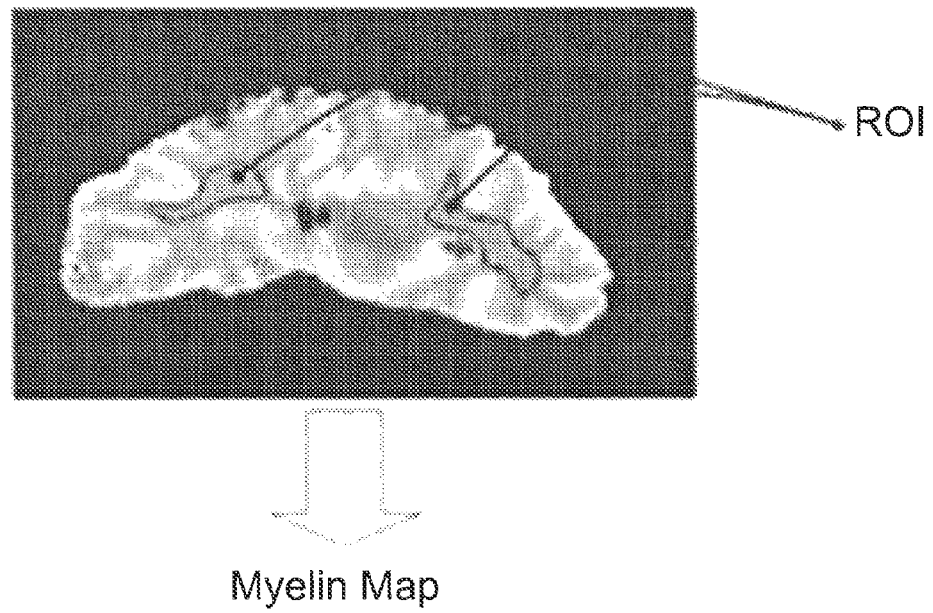
FIG. 11 shows the anatomical image of the fixed brain and its MWF obtained with optimal $t_1$ and $t_2$ values.
Figure 11:
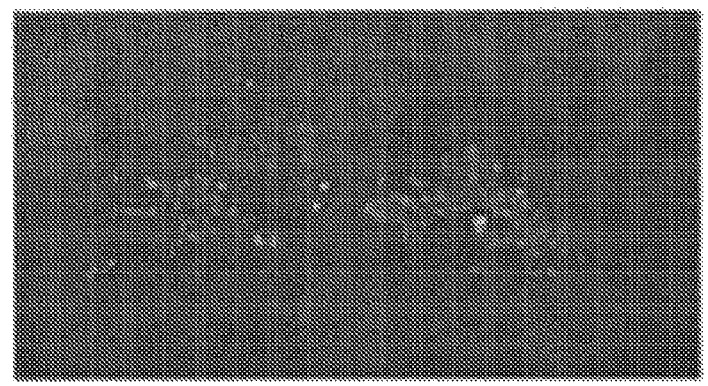
Figure 12:
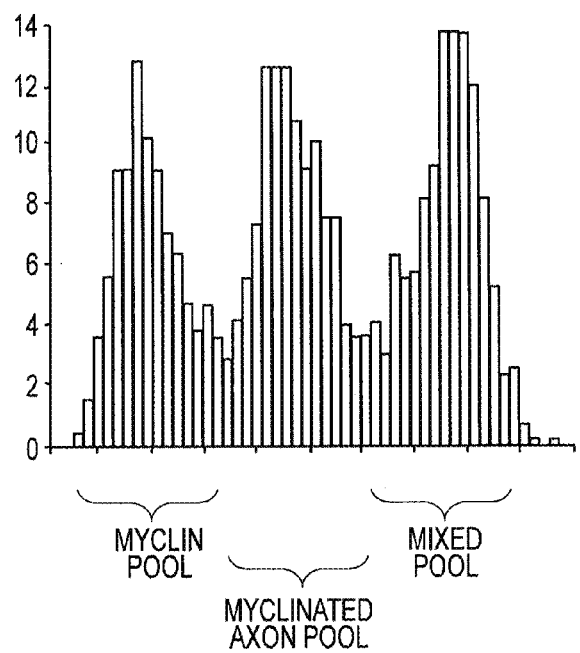
FIG. 12 shows the T2* distribution over the regions of interest in white matter that are depicted in FIG. 11 (top).
Figure 13:
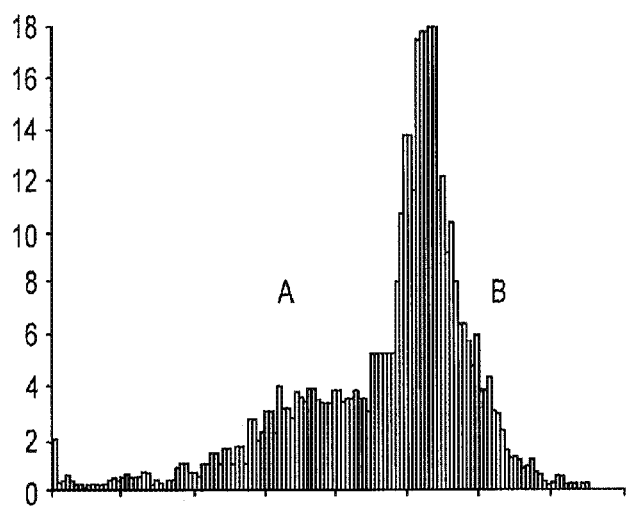
FIG. 13 shows the detected MWF histogram.
Figure 14:
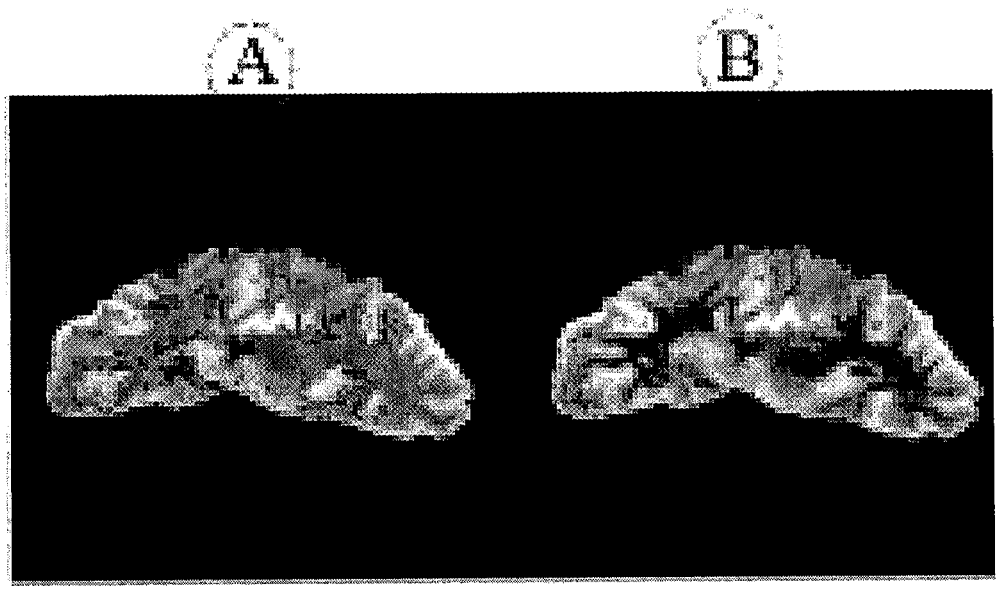
FIG. 14 shows pixels corresponding to the lobes shown in FIG. 13.
Figure 15:
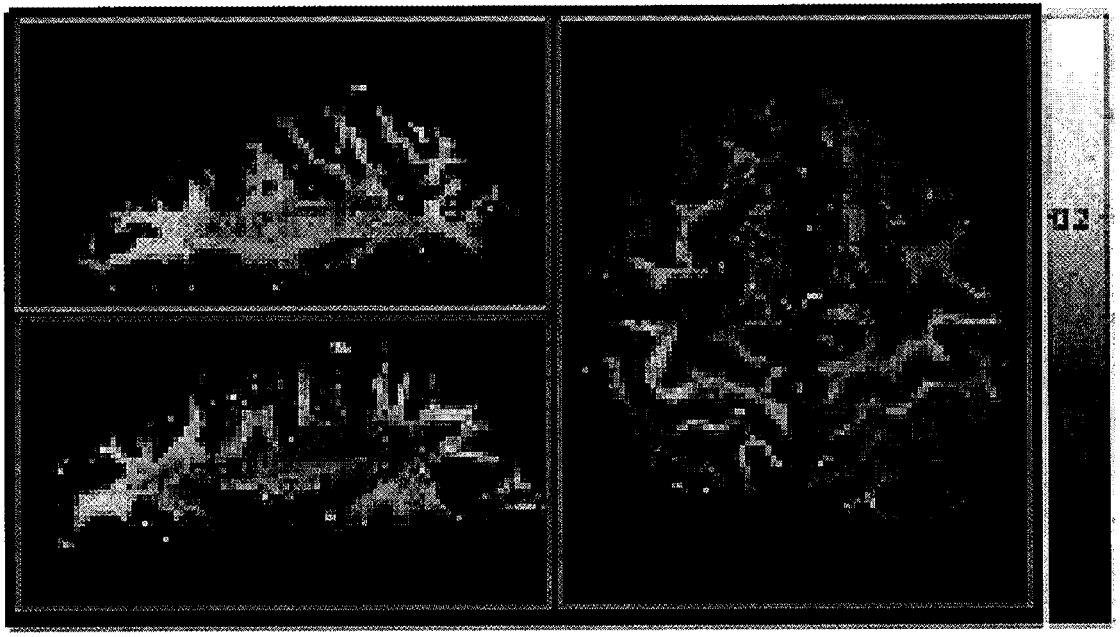
FIG. 15 shows the estimated MWF for other fixed brains.

FIG. 10 shows the average MWF measurement at a white matter region, its variation over $t_1$, and the fitting error for different $t_1$ values. The optimal $t_1$ is found to be at 16-20 ms. The same procedure was repeated to find the optimal $t_2$ value. FIG. 11 shows the anatomical image of the fixed brain (top) and its MWF (bottom) obtained with the optimal $t_1$ and $t_2$. FIG. 12 shows the T2* distribution over the regions of interest in white matter that are depicted in FIG. 9 (top). FIG. 12 clearly shows the three distinct peaks which correspond to the myelin (my) pool (3~16 ms), the myelinated axon (ma) pool (16~34 ms), and the mixed (mx) pool (34~45 ms), respectively. FIG. 12 shows the detected MWF histogram which has two separate lobes demoted by 'A' and 'B'. FIG. 14 left and right show pixels corresponding to 'A' and 'B' lobes, respectively. The MWF for most white matter ranges from 9~14% (lobe B) and the MWF of the edges between white and gray matter ranges from 4~8% (lobe A). FIG. 15 shows the estimated MWF for other fixed brains.

These results show that the three-pool model analysis with T2* relaxation can produce myelin maps based on MWF in human brain. Optimal selection of T2* ranges for the fitting of three pools was made and T2* distribution of the estimated myelin maps shows three distinct peaks corresponding to each of the three pools. T2* relaxation time in a pixel is related to T2 relaxation time by: 1/T2*=1/T2+1/T2', where 1/T2' is determined by mesoscopic field inhomogeneities. The T2' in WM at 3 Tesla is estimated to be approximately 100 ms, based on the documented T2 (79.6 ms) and T2* (44.8 ms) of WM. Assuming that T2' is the same in all three pools, the estimated T2* value would be 9.1 ms, 28.8 ms, and 57.3 ms in myelin, myelinated axon, and mixed pools, respectively.

Figure 2:
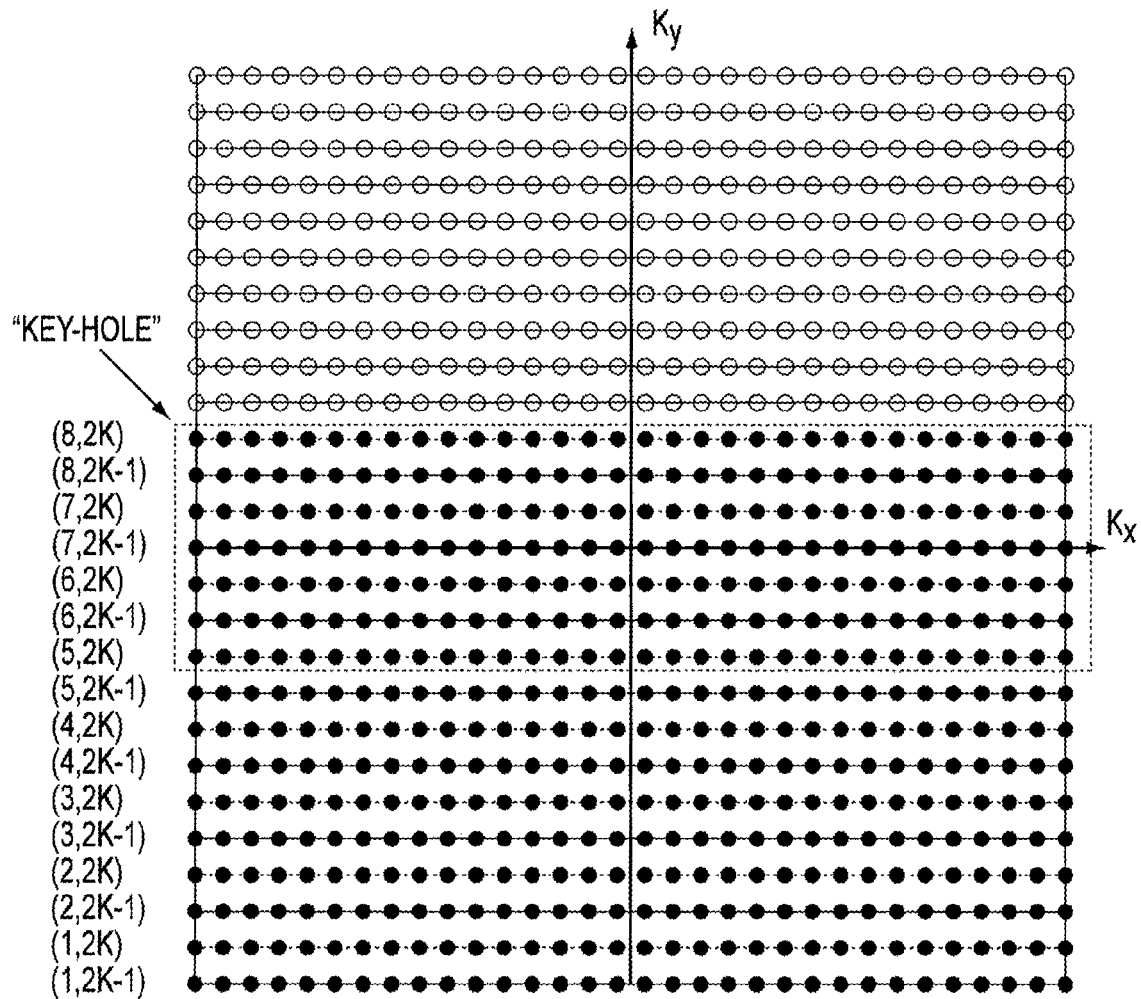
FIG. 2 is a diagram showing k-space of double ky line acquisition with partial ky and rectangular FOV for the kth image.

Imaging time for acquiring free induction decay signals in accordance with the present invention is significantly reduced by using a number of different methods including, but not limited to, dual ky-line acquisition, rectangular FOV acquisition, Half-Fourier acquisition, and "key-hole" acquisition strategy. Dual ky-line acquisition will allow two ky lines to be acquired in each excitation as shown in FIG. 2. The k-space of double ky line acquisition with partial ky and rectangular FOV for the kth image. Each ky line is indicated by (shot, echo). The (2k−1)th echoes (dark dots) and (2k)th echoes (grey dots) are used to reconstruct the kth image. For simplicity, this figure shows a k-space matrix of 32×26 for rectangular FOV and square-pixel acquisition. The sampling spacing is 1/FOVx along kx and 1/FOVy along ky. The partial ky acquisition has 3 ky over-sampling lines. The projection onto convex sets (POCS) algorithm will be used to fill the unsampled portion of the k-space, as shown in the open circles. "Key hole" acquisition will be used for averaging the date in the central k-space, as shown in the dashed rectangle. In the dual ky-line acquisition approach, the step size of the phase-encoding (PE) gradient is doubled. Alternating phase encoding blips are used to fill the missing ky lines. With this approach, the imaging time can be reduced by 50% and the sampling interval in the FID measurements are doubled (i.e. from 1.1 ms to 2.2 ms).

Rectangular FOV acquisition with a ratio of 22 cm:18 cm can reduce the imaging time by 18% with the phase-encoding along the R/L direction. An image matrix size of 256×210 is used in the data acquisition and the data is zero-filled to 256×256 prior to reconstruction. Using Half-Fourier data acquisition with 20 over-sampled ky lines can further reduce imaging time by 40%.

With key-hole acquisition strategy, the central ky lines in k-space (referred to as "key-hole" data) are acquired multiple times and then averaged prior to reconstruction. The data acquisition time for a "key-hole" dataset at the central 20 ky lines only takes 40 seconds at TR=2 sec. The approach of acquiring multiple datasets with minimal imaging time for each of the datasets enables removal of the datasets corrupted by severe head motion during data acquisition. In addition, physiological noise can be effectively reduced by using the above described approaches. The use of sensitivity encoding (SENSE) parallel imaging may also be explored in carrying out the fast multi-slice mapping of myelin water fraction in accordance with the present invention.

The over-estimation of MWF due to T1 partial saturation may also be corrected. Over-estimation of MWF can occur because the myelin water in the 3-pool analysis has much less T1 partial saturation than the other two pools due to its relatively short TR (eg. 2 sec). To correct this, consecutive MGRE scans with TR=0.5 s, 1 s, 2 s, 4 s, and 6 s with a 90 degree flip angle are performed. Multi-compartment analysis is applied to each dataset at each TR. The averaged signal of each pool, $A_j$, in the same ROI of the WM is calculated from the MGRE data acquired at these TRs. The T1 of each pool is obtained by fitting $A_j$ to: $A_j = M_{o,j} E_{1,j}$ where $E_{1,j} = \exp(-TR/T_{1,j})$, j=my, ma and mx; $M_{o,j}$ and $T_{1,j}$ are the water content and T1 in each pool, respectively. The MWF is calculated using the following equation with the correction of T1 partial saturation effect:

$$MWF = \frac{A_{my}(1/E_{1,my} - \cos\theta)}{A_{my}(1/E_{1,my} - \cos\theta) + A_{ma}(1/E_{1,ma} - \cos\theta) + A_{mx}(1/E_{1,mx} - \cos\theta)}$$

where θ is the flip angle.

Temporal filtering may be applied to the averaged MGRE datasets to further reduce the physiological noise. The Fourier transform is the first applied to the FID data along the time domain. Low-pass filtering, such as window filter or a Hamming filter, is applied to smooth out the temporal variation introduced by the physiological noise. Smoothed FID is obtained by applying inverse Fourier transform to the filtered data.

In addition to its application in the differentiation of demyelination and axonal damage in MS, the methods disclosed here may be used to detect and/or monitor the presence and progress of a disease or an injury in the central nervous system. The methods may also be used to test the effectiveness of a drug treatment or other clinical intervention for a disease or an injury in the central nervous system, and to assess brain development on a whole-brain or regional basis.

There has been evidence implicating aberrant myelination in the onset and/or progress of schizophrenia and Alzheimer's disease. MRI technology may permit in vivo assessment of the lifelong trajectory of human myelin development and its subsequent breakdown with minimal invasiveness. The methods disclosed herein may be used as a screening tool for schizophrenia or neuron-degenerative diseases such as Alzheimer's disease where early detection is of great clinical and social importance. The presently disclosed methods may also provide a framework for developing novel treatments, as well as assessing efficacy of currently available treatments, intended to slow or reverse the breakdown process in both clinically healthy as well as symptomatic populations.

Although an MRI field strength of about 2-7 Tesla is used as examples in this disclosure, the present disclosure encompasses using various MRI field strengths to obtain T2* measurements. Whether or not a particular T2* measurements indicate a specific disease state of an individual will depend on the MRI field strength used. However, the relationships between T2* measurements obtained using different field strengths is well known in the MRI research field. Therefore, the disclosed methods may be applied even when MRI field strength other than 2-7 Tesla is used.

It is to be understood that the methods for data acquisition and the multi-compartment analysis disclosed herein may be used independently from each other. It is also worth noting that the disclosed methodology may be applied to MRI analysis of body parts other than the central nervous system. While particular embodiments of the present disclosure have been shown and described, it may be obvious to those skilled in the art that, based upon the teachings herein, changes and modifications may be made without departing from the spirit of this invention and its broader aspects and, therefore, the appended claims are to encompass within their scope all such changes and modifications as are within the true spirit and scope of this invention.

The invention claimed is:

1. A method for early detection of white matter abnormality in the central nervous system comprising the steps of:
   acquiring free induction decay signals of a plurality of voxels at multiple slice locations in the central nervous system using an echo-planar spectroscopic imaging pulse sequence; and
   analyzing the free induction decay signals in a plurality of pixels corresponding to the plurality of voxels to obtain a quantitative map of myelin water fraction in the central nervous system using multi-compartment analysis,
   wherein the step of analyzing the free induction decay signals in a plurality of pixels corresponding to the plurality of voxels comprises the step of optimizing a selection of a range of signal decay constants for each compartment in the multi-compartment analysis.

2. The method of claim 1 wherein the central nervous system comprises at least one of a brain and a spinal cord.

3. The method of claim 1 wherein the step of analyzing the free induction decay signals comprises the step of using a 3-pool model of white matter.

4. The method of claim 3 wherein the 3-pool model comprises a myelin water pool, a myelinated axon water pool, and a mixed water pool.

5. The method of claim 1 wherein the step of acquiring free induction decay signals comprises acquiring free induction decay signals of a plurality of voxels at multiple slices.

6. The method of claim 1 wherein the step of acquiring free induction decay signals comprises the step of acquiring a train of multi-gradient echoes with alternating gradient polarities.

7. The method of claim 6 wherein the step of acquiring multiple multi-gradient echo datasets comprises the step of performing at least one of dual ky-line acquisition, rectangular FOV acquisition, half Fourier acquisition, and key-hole acquisition.

8. The method of claim 1 wherein the step of analyzing free induction decay signals comprises the step of averaging of multiple multi-gradient echo datasets to reduce physiological noise.

9. The method of claim 1 wherein the step of analyzing the free induction decay signals in a plurality of pixels corresponding to the plurality of voxels comprises the step of incorporating a local gradient compensation factor to correct for susceptibility-induced local gradients.

10. A method for monitoring the progression of white matter abnormality in the central nervous system comprising the steps of:
    acquiring free induction decay signals of a plurality of voxels at multiple slice locations in the central nervous system using an echo-planar spectroscopic imaging pulse sequence; and
    analyzing the free induction decay signals in a plurality of pixels corresponding to the plurality of voxels to obtain a quantitative map of myelin water fraction in the central nervous system using multi-compartment analysis;
    wherein the step of analyzing the free induction decay signals in a plurality of pixels corresponding to the plurality of voxels comprises the step of optimizing a selection of a range of signal decay constants for each compartment in the multi-compartment analysis.

11. The method of claim 10 wherein the central nervous system comprises at least one of a brain and a spinal cord.

12. The method of claim 10 wherein the step of analyzing the free induction decay signals comprises the step of using a 3-pool model of white matter.

13. The method of claim 12 wherein the 3-pool model comprises a myelin water pool, a myelinated axon water pool, and a mixed water pool.

14. The method of claim 10 wherein the step of acquiring free induction decay signals comprises acquiring free induction decay signals of a plurality of voxels at multiple slices.

15. The method of claim 10 wherein the step of acquiring free induction decay signals comprises the step of acquiring a train of multi-gradient echoes with alternating gradient polarities.

16. The method of claim 15 wherein the step of acquiring multiple multi-gradient echo datasets comprises the step of performing at least one of dual ky-line acquisition, rectangular FOV acquisition, half Fourier acquisition, and key-hole acquisition.

17. The method of claim 10 wherein the step of analyzing free induction decay signals comprises the step of averaging of multiple multi-gradient echo datasets to reduce physiological noise.

18. The method of claim 10 wherein the step of analyzing the free induction decay signals in a plurality of pixels corresponding to the plurality of voxels comprises the step of incorporating a local gradient compensation factor to correct for susceptibility-induced local gradients.

19. A method for monitoring the effectiveness of a therapeutic treatment for white matter abnormality of the central nervous system comprising:
    acquiring free induction decay signals of a plurality of voxels at multiple slice locations in the central nervous system using an echo-planar spectroscopic imaging pulse sequence; and
    analyzing the free induction decay signals in a plurality of pixels corresponding to the plurality of voxels to obtain a quantitative map of myelin water fraction in the central nervous system using multi-compartment analysis
    wherein the step of analyzing the free induction decay signals in a plurality of pixels corresponding to the plurality of voxels comprises the step of optimizing a selection of a range of signal decay constants for each compartment in the multi-compartment analysis.

20. The method of claim 19 wherein the central nervous system comprises at least one of a brain and a spinal cord.

21. The method of claim 19 wherein the step of analyzing the free induction decay signals comprises the step of using a 3-pool model of white matter.

22. The method of claim 21 wherein the 3-pool model comprises a myelin water pool, a myelinated axon water pool, and a mixed water pool.

23. The method of claim 19 wherein the step of acquiring free induction decay signals comprises acquiring free induction decay signals of a plurality of voxels at multiple slices.

24. The method of claim 19 wherein the step of acquiring free induction decay signals comprises the step of acquiring a train of multi-gradient echoes with alternating gradient polarities.

25. The method of claim 24 wherein the step of acquiring multiple multi-gradient echo datasets comprises the step of performing at least one of dual ky-line acquisition, rectangular FOV acquisition, half Fourier acquisition, and key-hole acquisition.

26. The method of claim 19 wherein the step of analyzing free induction decay signals comprises the step of averaging of multiple multi-gradient echo datasets to reduce physiological noise.

27. The method of claim 19 wherein the step of analyzing the free induction decay signals in a plurality of pixels corresponding to the plurality of voxels comprises the step of incorporating a local gradient compensation factor to correct for susceptibility-induced local gradients.

28. A method for determining a macromolecular content in a body organ of an individual comprising the steps of:
    acquiring free induction decay signals of a plurality of voxels at multiple slice locations in the body organ using an echo-planar spectroscopic imaging pulse sequence; and
    analyzing the free induction decay signals of each voxel to obtain a quantitative map of the macromolecular content in the body organ using multi-compartment analysis;
    wherein the step of analyzing the free induction decay signals of each voxel comprises the step of optimizing a selection of a range of signal decay constants for each compartment in the multi-compartment analysis.

29. The method of claim 28 wherein the step of acquiring free induction decay signals comprises the step of acquiring a train of multi-gradient echoes with alternating gradient polarities.

30. The method of claim 29 wherein the step of acquiring multiple multi-gradient echo datasets comprises the step of performing at least one of dual ky-line acquisition, rectangular FOV acquisition, half Fourier acquisition, and key-hole acquisition.

31. The method of claim 28 wherein the step of analyzing free induction decay signals comprises the step of averaging of multiple multi-gradient echo datasets to reduce physiological noise.

* * * * *